United States Patent
Sim et al.

(10) Patent No.: US 9,079,137 B2
(45) Date of Patent: Jul. 14, 2015

(54) METHOD AND APPARATUS FOR DETERMINING BIOFOULING OF A MEMBRANE

(71) Applicant: NANYANG TECHNOLOGICAL UNIVERSITY, Singapore (SG)

(72) Inventors: Victor Siang Tze Sim, Singapore (SG); Stanislaus Raditya Suwarno, Singapore (SG); Tzyy Haur Chong, Singapore (SG); Adrian Piah Song Yeo, Singapore (SG); William Bernard Krantz, Singapore (SG); Anthony Gordon Fane, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/354,924

(22) PCT Filed: Oct. 31, 2012

(86) PCT No.: PCT/SG2012/000411
§ 371 (c)(1),
(2) Date: Apr. 28, 2014

(87) PCT Pub. No.: WO2013/066268
PCT Pub. Date: May 10, 2013

(65) Prior Publication Data
US 2014/0254323 A1    Sep. 11, 2014

Related U.S. Application Data

(60) Provisional application No. 61/553,637, filed on Oct. 31, 2011.

(51) Int. Cl.
| | |
|---|---|
| *B01D 65/10* | (2006.01) |
| *G01N 29/32* | (2006.01) |
| *G01N 29/032* | (2006.01) |
| *G01N 29/22* | (2006.01) |
| *G01N 29/44* | (2006.01) |
| *B01D 61/12* | (2006.01) |

(52) U.S. Cl.
CPC ............... *B01D 65/10* (2013.01); *B01D 61/12* (2013.01); *G01N 29/032* (2013.01); *G01N 29/222* (2013.01); *G01N 29/4454* (2013.01); *G01N 2291/0258* (2013.01); *G01N 2291/044* (2013.01)

(58) Field of Classification Search
CPC ..................................................... G01N 29/032
USPC ............................................................. 367/13
See application file for complete search history.

(56) References Cited

U.S. PATENT DOCUMENTS

| | | | | |
|---|---|---|---|---|
| 6,161,435 | A * | 12/2000 | Bond et al. ....................... | 73/587 |
| 8,210,042 | B2 * | 7/2012 | Mickols et al. .................. | 73/587 |
| 2014/0254323 | A1 * | 9/2014 | Sim et al. ......................... | 367/87 |

FOREIGN PATENT DOCUMENTS

| | | |
|---|---|---|
| WO | 2008103864 A2 | 8/2008 |
| WO | 2013066268 A1 | 5/2013 |
| ZA | 200404213 A | 4/2006 |

OTHER PUBLICATIONS

Foreign Communication from a Related Counterpart Application, International Search Report and Written Opinion dated Jan. 3, 2013, International Application No. PCT/SG2012/000411 filed on Oct. 31, 2012.

*Primary Examiner* — Daniel Pihulic (57) ABSTRACT

A method of determining a state of biofouling of a membrane is provided. The membrane is contained within a flow cell and the flow cell has an outer surface coupled to a tranducer, The method comprises introducing inorganic particles into the flow cell such that the inorganic particles form a part of a top surface of a foulant layer on the membrane. The transducer then emits acoustic waves towards the membrane and an acoustic signature of reflected sound waves are detected. A state of biofouling of the membrane is determined based on the detected acoustic signature. A method and an apparatus are also provided for determining a state of biofouling in commercial membrane modules such as spiral wounded membrane modules.

28 Claims, 8 Drawing Sheets

METHOD AND APPARATUS FOR DETERMINING BIOFOULING OF A MEMBRANE

CROSS-REFERENCE TO RELATED APPLICATIONS

This application is a filing under 35 U.S.C. 371 as the National Stage of International Application No. PCT/SG2012/000411, filed Oct. 31, 2012, entitled "METHOD AND APPARATUS FOR DETERMINING BIOFOULING OF A MEMBRANE", which claims the benefit of and priority to U.S. Provisional Patent Application No. 61/553,637, filed Oct. 31, 2011 and entitled "METHOD AND APPARATUS FOR DETERMINING BIOFOULING OF A MEMBRANE", both of which are incorporated herein by reference in their entirety for all purposes.

TECHNICAL FIELD

The present invention relates to a method and an apparatus for determining a state of biofouling of a membrane. This method can be used in, but is not limited to, liquid separation processes that use membrane modules.

BACKGROUND

There is a steady increase globally in the installation of reverse osmosis (RO) desalination plants. Simultaneously there is a growing concern about energy for desalination. Membrane fouling is potentially a major inefficiency in a desalination (and reclamation) plant and the reduced permeability produces an unwanted increase in energy demand as well as costly shut down and membrane replacement.

Biofouling is widely recognized as the major fouling issue in both RO desalination and reclamation plants. Current pretreatment options could not eliminate biofilm formation in the membrane modules, each of which consists of multiple membrane layers and, feed and permeate channel spacers. As a result, productivity is reduced or more energy is required to maintain the production, and the salt passage through the membrane modules is aggravated. The lack of suitable techniques sensitive enough for studying and/or detecting membrane biofouling under realistic operating conditions has hindered the development of appropriate strategies to control biofouling, which is critical for the sustainability of RO membrane technology.

Conventional techniques such as monitoring the transmembrane pressure profile under constant flux operation or the flux profile under constant pressure operation, quality of permeate and microbial monitoring suffer from one or more disadvantages such as low sensitivity or long response time to detect incipient fouling. U.S. Pat. No. 6,161,435 (Bond et al.) describes an acoustic detection technique for the initiation of membrane fouling as well as the state of membrane fouling and the rate of membrane fouling to provide an early warning that permits adjusting the system operating parameters to mitigate the fouling problem. It uses the propagation of acoustic waves via compression and rarefaction to give information on the physical characteristics of the media through which the waves travel. However, it has very limited applicability for detecting biological or organic fouling in membrane processes. In particular, Bond et al. is not able to detect the initiation of membrane biofouling, the state of biofouling or the rate of biofouling caused by biological and/or organic foulants.

Furthermore, employing the apparatus of Bond et al. on commercial spiral wound modules is very costly given the huge number of transducers required to cover an appropriate effective membrane area for each spiral wound module multiplied by the significant number of modules used in a typical desalination or reclamation plant. This is further aggravated by the sheer complexity of the resultant acoustic signature from multiple reflections of the membranes, spacers and supports, resulting in lower sensitivity due to the increased superimposition of transmitted and reflected waveforms. It is also required for the transducer to be custom-made made due to the surface configuration of the spiral wound module.

SUMMARY

The present invention proposes a novel improved acoustic method of determining a state of biofouling/organic fouling of a membrane. The method may be used for characterizing biofouling propensity, incipient biofouling and/or the state of cleaning of the membrane The invention further proposes a method of determining the state of biofouling of a membrane module, such as that used in liquid separation processes. The membrane module may be a commercial high-pressure membrane module such as spiral wound membrane modules and hollow fiber membrane modules. An ancillary flow cell employing the novel method above of determining a state of biofouling/organic fouling of a membrane is configured to foul sooner than that of the commercial membrane module so as to provide timely warnings for controlling biofouling of the membrane module during the filtration process. Accordingly, the state of biofouling in the commercial membrane module may be determined indirectly by the biofouling state of the ancillary flow cell with high sensitivity at a low cost.

According to a first aspect, there is provided a method of determining a state of biofouling of a membrane contained within a flow cell, the flow cell having at least an outer surface coupled to one or more acoustic transducers, the method comprising the following steps:

introducing inorganic particles into the flow cell such that the inorganic particles form at least a part of a top surface of a foulant layer on the membrane;

emitting acoustic waves towards the membrane using the one or more transducers;

detecting an acoustic signature of reflected sound waves, the acoustic signature comprising a profile of reflected sound waves from the top surface and a profile of reflected waves from the membrane; and determining, based on the detected acoustic signature, a state of biofouling of the membrane.

The membrane may be a flat sheet membrane.

In one embodiment, the acoustic signature further comprises a profile of reflected sound waves from a reference point. Typically, the step of determining comprises comparing the profile of reflected sound waves from the top surface and the profile of reflected sound waves from the membrane against the profile of reflected sound wave from the reference point.

Preferably, the step of determining further comprises analysing the acoustic signature using ultrasonic time domain reflectometry. The state of biofouling may comprise a thickness of the foulant layer, the rate at which biofouling occurs, and/or the amount of membrane compaction.

Typically, the inorganic particles comprise particles capable of enhancing an acoustic impedance difference between the foulant layer and the membrane. Preferably, the inorganic particles comprise particles capable of enhancing an acoustic impedance difference between the foulant layer and the feed solution. In one embodiment, the inorganic particles comprise at least one of: silica particles, nanoparticles, glass beads, and a colloidal insoluble compound.

The step of introducing inorganic particles may comprise one of: intermittently injecting, partially injecting and continuously injecting the inorganic particles.

In one embodiment, the acoustic transducer is a focused transducer.

In another embodiment, the method further comprises a step of removing the inorganic particles from the flow cell. This step may be repeated with any embodiments of the above method.

According to a second aspect, there is provided a method of determining a state of biofouling of a first membrane in a membrane module, the method comprising the steps of:

providing an ancillary flow cell comprising a second membrane in parallel with the membrane module;

diverting part of a feed stream for the membrane module as a side stream into the ancillary flow cell;

introducing inorganic particles into the ancillary flow cell such that the inorganic particles form at least a part of a top surface of a foulant layer formed on the second membrane due to the side stream;

emitting acoustic waves towards the second membrane using at least one transducer;

detecting an acoustic signature of reflected acoustic waves, the acoustic signature comprising a profile of reflected sound waves from the top surface and a profile of reflected sound waves from the second membrane;

determining, based on the detected acoustic signature, a state of biofouling of the second membrane; and configuring the ancillary flow cell relative to the membrane module such that a state of biofouling of the ancillary flow cell is indicative of a state of biofouling of the first membrane in the membrane module.

Preferably, the second membrane is a flat sheet membrane.

In one embodiment, the acoustic signature further comprises a profile of reflected sound waves from a reference point. Typically, the step of determining comprises comparing the profile of reflected sound waves from the top surface and the profile of reflected sound waves from the membrane against the profile of reflected sound wave from the reference point. Optionally, the step of determining further comprises analysing the acoustic signature using ultrasonic time domain reflectometry.

Typically, the state of biofouling comprises a thickness of the foulant layer, the rate at which biofouling occurs, and/or the amount of membrane compaction. Preferably, the inorganic particles comprise particles capable of enhancing an acoustic impedance difference between the foulant layer and the second membrane.

In one embodiment, the membrane module is a spiral wound module or a hollow fiber membrane module.

In a preferred embodiment, the ancillary flow cell is configured to foul earlier than the membrane module. The method may further comprise removing the inorganic particles from the ancillary flow cell.

According to a third aspect, there is provided an apparatus for determining a state of biofouling of a first membrane in a membrane module, the apparatus comprising:

an ancillary flow cell configured to receive part of a feed stream diverted from the membrane module, the ancillary flow cell comprising a second membrane provided in a compartment defined between a top plate and a bottom plate;

inorganic particles configured to be introduced into the ancillary flow cell to form at least a part of a top surface of a foulant layer formed on the second membrane;

at least one transducer provided on at least one of: the top plate and the bottom plate, the at least one transducer configured to emit acoustic waves towards the second membrane and to receive reflected waves from the top surface and reflected waves from the second membrane; and an analysis module configured to perform acoustic reflectometry measurements and to determine a state of biofouling of the ancillary flow cell based on acoustic signatures of the reflected waves from the top surface and reflected waves from the second membrane;

such that a state of biofouling of the ancillary flow cell is indicative of a state of biofouling of the first membrane in the membrane module.

Preferably, the second membrane is a flat sheet membrane.

Typically, the state of biofouling comprises a thickness of the foulant layer, the rate at which biofouling occurs, and/or the amount of membrane compaction. Typically, the inorganic particles comprise particles capable of enhancing an acoustic impedance difference between the foulant layer and the second membrane.

In a preferred embodiment, the ancillary flow cell is configured to foul earlier than the membrane module.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings.

In the drawings:

FIG. 7(a) is a graph of fouling layer thickness determined via UTDR during a dosing and flushing procedure as a function of contact times in days for a crossflow velocity of 0.15 m/s, a constant flux of 35 LMH, an aqueous sodium chloride solution of 2 g/L, dilution factor of 500 for model bacteria and a dosing of silica concentration of 0.2 g/L at initiation of a biofouling experiment;

FIG. 7 (b) is a graph of fouling layer thickness determined via UTDR during the dosing and flushing procedure as for FIG. 7 (a) at end of the biofouling experiment;

FIG. 8 (a) is a graph of fouling layer thickness determined via UTDR during a dosing and flushing procedure as a function of contact time in days for a crossflow velocity of 0.13 m/s, a constant flux of 40 LMH, an aqueous sodium chloride solution of 2 g/L, dilution factor of 500 for model bacteria and a dosing of silica concentration of 0.2 g/L at initiation of biofouling experiment;

FIG. 8 (b) is a graph of fouling layer thickness determined via UTDR during the dosing and flushing procedure as for FIG. 8 (a) at end of the biofouling experiment;

DETAILED DESCRIPTION

Exemplary embodiments of a method 10 for detecting biofouling in membrane processes will be described with reference to FIGS. 1 to 12 below.

Figure 12:
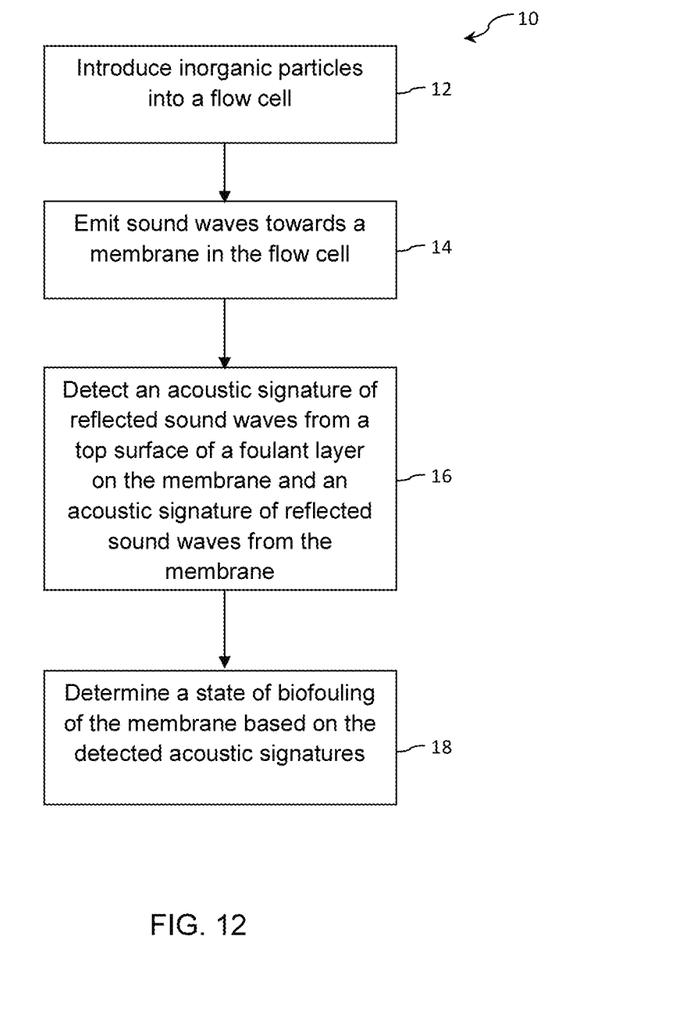
FIG. 12 is a flowchart of an exemplary method of the present invention.

The method 10 (as shown in FIG. 12) involves using sensor technology based on acoustic reflectometry together with inorganic particles as tracers to enhance detection sensitivity. Possible types of acoustic reflectometry that may be used include ultrasound time-domain reflectometry (UTDR) and ultrasound frequency domain reflectometry (UFDR). Below, the fundamental principles of UTDR measurement are explained as an example to facilitate understanding of the method 10. However, a skilled person in the art will appreciate that UFDR and other types of acoustic reflectometry may be similarly used to detect membrane fouling. UTDR should therefore not be construed as the only embodiment applicable to the method of the present invention.

In an exemplary embodiment, the method 10 uses a flow cell 100 as shown in FIG. 1(a). The flow cell 100 has at least an outer surface coupled to a transducer 106. In an alternative embodiment, more than one transducer 106 may be used. The transducer 106 is used for generating and receiving acoustic waveforms through vibrations of piezoelectric crystals excited from electrical energy emitted from a signal pulser and receiver. In this embodiment, the flow cell 100 is a flat-sheet module having a flat sheet membrane 108. Membranes/membrane modules in any other configurations are also possible to be used in the method 10. For example, a membrane/membrane module in a hollow fibre configuration. The flow cell 100 comprises an acoustic transducer 106 housed in a compartment above a top plate 102. In an alternative embodiment, the transducer 106 may be housed below a bottom plate 104. The transducer 106 is preferably an ultrasonic transducer. The flow cell 100 further comprises a second compartment in which a feed solution 101 is flowed and in which an appropriately sealed and supported filtration membrane 108 is provided between the top plate 102 and the bottom plate 104. The top 102 or bottom plate 104 may partially or wholly consist of a material that minimizes acoustic attenuation, such as acrylic, glass or fine-grain steel, but is not limited to the aforementioned materials.

The flow cell 100 is suitable for high pressure applications. For example, the flow cell 100 is may be configured to withstand a pressure up to 4 MPa bar (580.2 psig) and above. A support plate 110 may be provided for the filtration membrane 108. Preferably, the support plate 110 is rigid and is permeable to fluid and/or gas. The support plate 110 may comprise a sintered metal, ceramic or polymer particle membrane, perforated metal, ceramic or polymer plate, metal, ceramic or polymer screen, and/or any other highly permeable and rigid supporting structure.

The method 10 comprises introducing inorganic particles (not shown) into the flow cell 100, 12. In particular, this step 12 involves dosing or injecting of any appropriate particles such as, but not limited to, silica, nano-particles, glass beads and/or colloidal insoluble compounds. Appropriate particles include particles that can artificially enhance the acoustic impedance difference between the biofouling layer and membrane, and/or between the layer and feed solution. The inorganic particles may be introduced into the flow cell 100 intermittently, partially and/or continuously. For example, the particles may be injected as a one-time spike or several times at periodic intervals. In a particular example, the particles are injected via a port (not shown) operating in series with the flow cell 100 and/or together with the feed solution 101.

The particles that are injected in this invention in order to enhance the reflection of the ultrasound signal can be composed of either an inorganic or organic material or a composite of these materials. In order to enhance the reflection of the ultrasound signal, the particles should be more dense than water. The particles need to be sufficiently small to be incorporated in reasonably large numbers within the biofouling layer. Since the particles are more dense than water, they need to be sufficiently small to avoid gravitational settling out during operation; that is, they should be sufficiently small to be kept in suspension by the flow of the water through the device described in this invention. The colloidal particles used in the proof-of-concept had a diameter of 20 nanometers. However, particles having a diameter on the order of 1 to 100 nanometers can be used. The particles preferably do not have any biocidal effects that would affect the viability of the biofouling layer. It is also preferred that the particles do not interact with the biofilm in any way that would change the nature of the biofouling process. In order to be used in aqueous systems for which biofouling occurs, it is desirable for the particles to be hydrophilic or water-wet; that is, have the property of being readily dispersable in water. However, it is preferred that the particles are not soluble in water. In order to permit easy flushing and disposal of the particles, it is desirable that they are non-toxic. Since the particles are expendable, it is desirable that they are inexpensive.

As a result, the inorganic particles form at least a part of a top surface 119 of a foulant layer 118 existing on the membrane 108. For example, the inorganic particles may form an immediate layer 119 above the original foulant layer 118, or percolate within the foulant layer 118 to artificially enhance the acoustic impedance difference when compared to the initial biological or organic foulant layer 118.

The method 10 further comprises emitting acoustic or sound waves directed towards the membrane 108 using the tranducer 106, 14 during UTDR measurement. The velocity c of the emitted acoustic wave travelling in a medium (material) is determined by the property of that material in which the wave is being transmitted. The velocity c of the acoustic wave increases with increasing density p of the material. When an acoustic wave encounters an interface between two media, reflection, transmission, and mode conversion such as change of phase (i.e., of the waveform) can occur. The magnitude of the reflected and transmitted waves is a function of the difference between the acoustic impedance of the media, $Z_2-Z_1$, where $Z_i \equiv \rho_i c_i$ and the subscripts 1 and 2 denote the media from which and into which, respectively, the wave is propagating. In particular, the amplitude A of the reflected wave relative to that of the incident wave perpendicular to an interface is given by, $$A = \frac{Z_2 - Z_1}{Z_2 + Z_1} \quad (1)$$

Accordingly, if the acoustic impedances of the two media are very similar, the interface of the two media behaves as if it is totally transparent to the sound waves and does not result in any significant reflection or mode conversion (i.e. amplitude A is very small). On the other hand, if the acoustic impedance difference between the two media is bigger, a more significant fraction of incident wave will be reflected back.

The time, t, required for a wave to travel to and back from a reflecting interface is a function of the distance between the reflecting interface and the transducer, Δd, and the velocity at which the wave is travelling. This is given by $$t = \frac{2\Delta d}{c} \quad (2)$$

Upon the transducer 106 emitting the acoustic waves towards the membrane 108, an acoustic signature of reflected sound waves is detected 16. An acoustic signature is a characteristic profile of reflected sounds waves from an object of interest, and may be obtained using acoustic reflectometry measurement. For example, the acoustic signature of the UTDR measurement provides direct information of the arrival time, amplitude, and phase modulation of the reflected waves. If an UFDR measurement is used, the acostic signature may comprise the frequency response.

Figure 4:
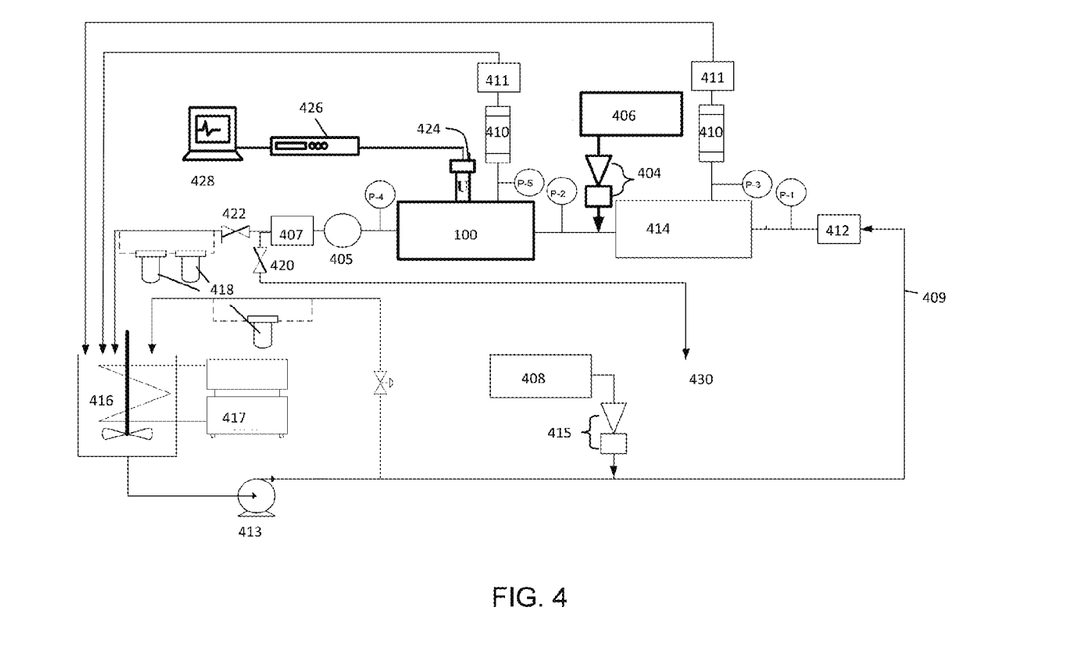
FIG. 4 is a schematic representation an experimental set-up used to demonstrate the present invention.

In the present embodiment, the acoustic signature comprises a profile of reflected sound waves from the top surface 119 of the foulant layer 118, and a profile of reflected sound waves from the membrane 108. The acoustic signature is depicted as observable waveforms of signal voltages in FIG. 1(b) which shows corresponding time-domain responses 112, 116, 114 in terms of the instantaneous voltage of the reflected sound waves as a function of time for the set-up in FIG. 1(a). The waveforms of signal voltages may be recorded by a storage oscilloscope 428 as shown in FIG. 4.

Based on the detected acoustic signature, a state of biofouling of the membrane 108 can then be determined 18. Referring to FIGS. 1(a) and 1(b), peak 112 is a stationary reference point, being a bottom surface 103 of the top plate 102. Arrival time of peaks 114 and 116 can be used to determine a thickness of the fouling layer 118 or the amount of compaction of the membrane 108 and/or the fouling layer 118. This is assuming that the velocity of sound in the feed solution is known. In the present embodiment, the velocity of sound in the feed solution is approximated to that of sound in water. For example, by superimposing the waveforms, a difference in arrival time between reference 112 and test 114, 116 waveforms can be compared using suitable software, and analysis may be performed to allow other physical characteristics to be determined. Examples of such characteristics are thickness of the foulant layer 118, a rate of fouling and/or the amount of membrane compaction. It should be noted that such information may also be derived from UFDR measurement in a similar manner, as will be understood by the skilled person in the art.

The method 10 described above provides substantial technical advantages over the prior art. In particular, the use of inorganic or other appropriate particles artificially enhances the overall acoustic differences between biological or organic foulants layer/membrane, and/or the foulant layer/feed solution interfaces and permits optimizing the sensitivity of detection method 10.

For example, when compared to the conventional UTDR as disclosed by Bond et al., the present invention 10 enables determining of a state of biofouling by artificially introducing inorganic particles as "tracers". As highlighted earlier, if the acoustic impedances of the two media are very similar, the interface of the two media behaves as if it is totally transparent to the sound waves and does not result in any significant reflection or mode conversion (i.e. amplitude A is very small). Essentially, if that is this case, the capacity and sensitivity of acoustic reflectometry to detect any reflected waves will be rather limited.

Since the bulk (around 70%) of biofilms or microbes are of a same composition as their surrounding water medium, the interface between them and the surrounding is bound to be very small. Similarly, as evident from the colloidal behaviour of macromolecular organic foulants, they also possess an acoustic impedance similar to that of water given their high water content. Therefore, when only UTDR is directly employed to detect a state of biofouling, hardly any signal can be detected.

In particular, without the introduction of inorganic particles into the flow cell 100, if the fouling layer 118 is caused by foulants that are biological or organic in nature, either the peak 114 does not shift/change; or, if a focused transducer is used, the peak 116 does not result. However, when inorganic particles are dosed just for a short period of time, the difference in acoustic impedance between the inorganic particles and surrounding medium are significantly enhanced. This causes the appearance of peak 116 or the change/shift in peak 114 depending on the use of either a focused or unfocused acoustic transducer 106. The inorganic particles either form an immediate layer as a top surface 119 above the original foulant layer 118 or percolate within the layer 118 to artificially enhance the acoustic impedance difference when compared to the initial biological or organic foulant layer 118 alone.

Focused transducers have a focal length which is the distance from the face of the transducer to the point in the sound field where the signal with the maximum amplitude is located. In an unfocused transducer, the focal length occurs at a distance from the face of the transducer which is approximately equivalent to the transducer's near field length and usually confers lesser resolution and sensitivity. In general, a focused transducer is more sensitive than an unfocused transducer while the unfocused one provides a larger field of view (FOV). While both types of transducer may be used for the purpose of the present invention, one type may be preferred than the other depending on a specific application.

Additionally, the method 10 may further comprise a step of removing the inorganic particles from the flow cell 100 after the measurement or determining of the state of biofouling of the membrane 108 is completed. For example, upon stoppage of the dosing of the inorganic particles, the inorganic particles are quickly removed from the foulant layer 118 either via back diffusion and/or shear-enhanced diffusion without significantly affect the membrane processes and/or the behaviour of the original biofoulant layer 118. Therefore, repeated cycles of dosing, measurement, and flushing (where flushing is draining of the flow cell 100 after dosing of the inorganic particles for removing the inorganic particles) may be performed to continuously monitoring the membrane biofouling process.

Figure 1:
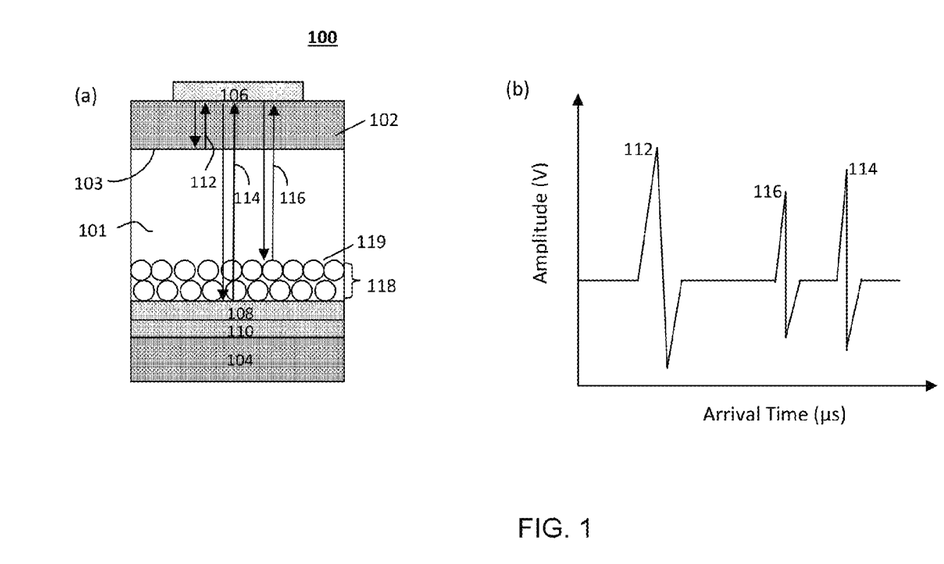
FIG. 1(a) is a schematic representation of the principle of UTDR measurements in a flow cell having a flat-sheet membrane.
FIG. 1(b) is a graph of corresponding time-domain responses for the flow cell of FIG. 1(a)
Figure 2:
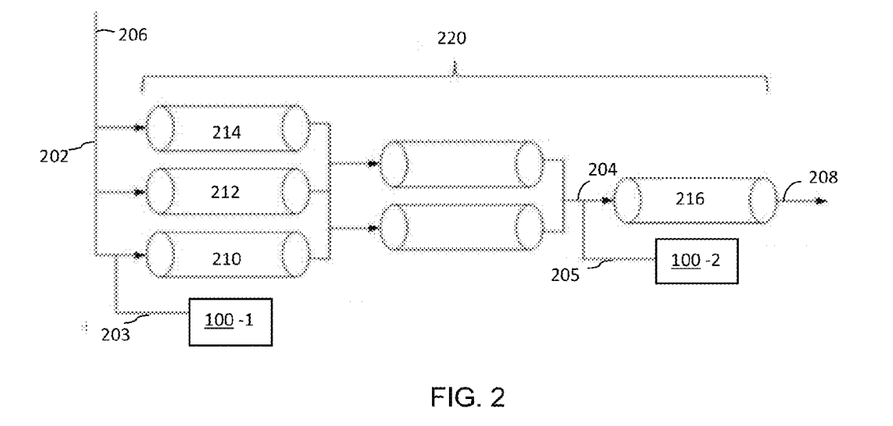
FIG. 2 is a schematic representation of ancillary flow cells for a 6-vessel RO train membrane module for performing the method of the present invention.
Figure 3:
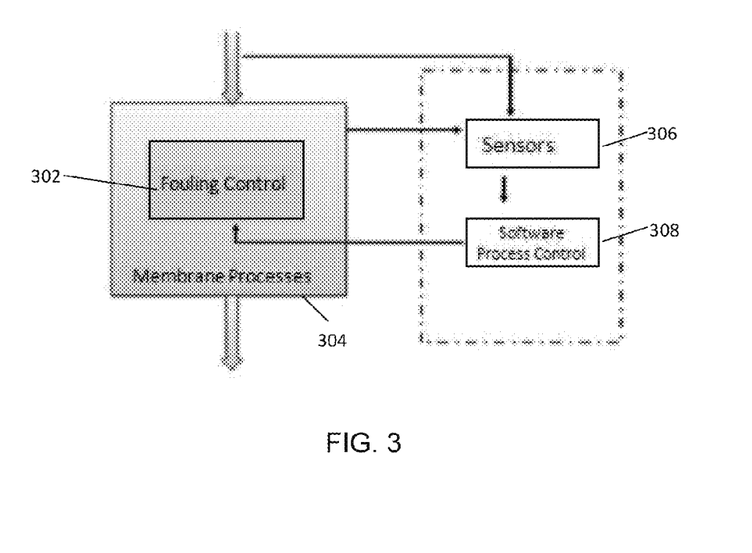
FIG. 3 is a schematic representation of a decision support system (DSS)

The method 10 is particularly suited to determining the state of biofouling of membrane modules 210, 212, 214, 216 in an RO train 220 as shown in FIG. 2. The membrane modules 210, 212, 214, 216 may be commercial high-pressure membrane modules such as spiral wound membrane modules, hollow fiber membrane modules and/or other membrane modules. In this application, in the RO train, a flow cell 100 is provided as an ancillary flow cell 100-1 comprising a membrane in parallel with the membrane modules 210, 212, 214. The membrane of the flow cell 100-1 may be in any configurations such as, but is not limited to a flat sheet or a hollow fiber configuration. Preferably, the membrane of the flow cell 100-1 is a flat sheet membrane. Part of a feed stream 202 for the membrane modules 210, 212, 214 is diverted as a side stream 203 into the ancillary flow cell 100-1. In the ancillary flow cell 100-1, the steps 12, 14, 16 and 18 of the method 10 as described above are performed in order to determine a state of biofouling of the membrane 108 in the ancillary flow cell 100-1.

The ancillary flow cell 100-1 may be configured to simulate fouling conditions in the one or more of the membrane modules 210, 212, 214. Another ancillary flow cell 100-2 may be provided downstream of the membrane modules 210, 212, 214 to receive a side stream 205 diverted from a feed stream 204 for a downstream membrane module 216. Thus, one or more ancillary flow cells 100 may be provided to receive side streams which are diverted from various feed streams of the commercial membrane modules in an RO train 220, so as to perform the method 10 for determining a state of biofouling of the membrane modules to which they are provided in parallel. The ancillary flow cell 100 thus functions as an acoustic "canary cell." The term "canary cell" used here is a colloquial term derived from the use of canaries in tunnel-mining operations to indicate the presence of toxic gases. The term 'canary cell' is thus used to describe a device that provides a warning of some type. In the present invention, it refers to a relatively small ancillary flow cell 100 that intercepts a slip or side stream from a water-treatment process. This invention employs ultrasound or acoustic waves emission and reflection accompanied by particle injection in order to detect biofouling in the canary cell 100, which then provides a warning that biofouling could be occurring in the membrane modules used in the water-treatment process.

The ancillary flow cell or canary cell 100 is thus preferably configured to foul earlier than that of the membrane modules so as to provide timely warnings of a state of biofouling of the membrane modules during the liquid separation processes. Accordingly, the state of biofouling in the membrane modules may be determined indirectly by the biofouling state of the ancillary flow cell 100 with high sensitivity at a low cost.

In the RO train described above, flow conditions in the canary cells 100-1, 100-2 are preferably controlled in relation to the membrane modules 210, 212, 214 and 216 respectively such that the fouling conditions of the canary cells 100-1, 100-2 are indicative of that of the membrane modules 210, 212, 214 and 216 respectively. In this example, the fouling condition of canary cell 100-1 is configured to resemble that of one or more of the spiral wound modules 210, 212, 214 in the RO train 220. Similarly, the fouling condition of canary cell 100-2 is configured to resemble that of the spiral wound module 216 in the RO train 220. In particular, computer modeling of hydrodynamics may be performed to predict a corresponding relationship of the flow conditions in the membrane modules and in the canary cells in order to obtain similar fouling conditions. Alternatively, such relationships may be established empirically. For example, through the control of fluxes and crossflow velocities, fouling behavior could be obtained in the canary cell 100-1, 100-2 that substantially models that of its corresponding membrane module 210, 212, 214 and 216 respectively. Advantageously, the canary cells 100-1, 100-2 can be versatile in simulating different fouling behavior within a spiral wound module, given that different fouling behavior may be found within the same spiral wound module.

In the prior art, when an acoustic transducer is directly used on a spiral wound module and without introducing any inorganic particles into the feed solution, there will be multiple repetitions of different peaks 116, 114 corresponding to multiple membrane leafs, supports, and spacers. As a result, the acoustic signature including shifts in arrival time and/or changes in acoustic impedances is blurred. For example, the peaks 116, 114 may superimpose instead of appearing as singly detectable peaks. Therefore, poor signal strength and limited sensitivity are to be expected in the prior art method.

Advantageously, the method 10 offers better sensitivity to detect incipient biofouling from the significantly less complex acoustic signature used in prior art. This is complemented with a reduction in the required number of acoustic transducers depending on the ratio of the acoustic canary cell's effective membrane surface area to the outer surface area of the spiral wound module. Moreover, adapting acoustic transducers for spiral wound membrane modules does not require special modifications in the present method.

One or more aspects of the present invention may be incorporated into an integrated control system to control biofouling 302 in membrane systems 304. For example, the method may be integrated with any software-based management system such as a Decision Support System (DSS) shown in FIG. 3. This may be further complemented by advanced data assimilation and optimization schemes to enhance process forecasting and optimization. Specifically, the state of biofouling detected or determined by the sensors 306 or flow cell 100 of the present method 10 characterizes incipient biofouling, biofouling propensity, and/or rate of biofouling. This information may be input to the software 308 to adjust membrane process operation to minimize the effect of biofouling and/or limit energy usage during filtration or cleaning processes.

Experimental Setup and Methodology

The following experiment was conducted to demonstrate the sensitivity and accuracy of the method 10 described above. This experimental setup described below should not be construed as limiting the scope of the implementation of the proposed method 10. Some components in the setup are essential while the rest are merely optional. In actual implementation of the method 10, the essential components are only those necessary for performing acoustic reflectometry measurements and a means for dosing any appropriate inorganic particles. For example, in this particular experiment, a transducer, a receiver and an oscilloscope were used for UTDR measurement and colloidal silica was dosed via an injection pump.

As shown in FIG. 4, a flow cell 100 containing a RO membrane is arranged in series with an injection port 404 or opening for introducing inorganic particles 406 into the flow cell 100. In this particular example, the RO membrane is a flat sheet membrane. A back pressure regulator 405 and a flow meter 407 are provided in between the flow cell 100 and two valves 420 and 422. A reference flow cell 414 is provided upstream of the injection port 404 as a control flow cell without injection of inorganic particles. A sensor 412 is provided before the reference flow cell 414 to measure the feed conductivity of feed solution 409. Representative data for performance of the present invention were taken for an aqueous feed stream containing model bacteria *Pseudomonas aeruginosa* that were chosen for this study as this strain has been commonly used in other biofilm studies. A bacteria stock solution 408 used in biofouling tests was prepared in batches and was replenished every 24 hours. A pump 415 was used for injecting the bacterial solution into the feed solution 409. The study was conducted in a constant flux mode and biofouling was measured via a rise in trans-membrane pressure (TMP). A sensor 411 for measuring permeate conductivity and a mass-flow controller 410 (Brooks Instrument, model 5882) was installed at a permeate side of each of the flow cell 100 and the reference flow cell 414 to maintain the amount of permeate withdrawn. The feed solution 409 is pumped out from a feed tank 416 via an injection jump 413, and the bacteria stock solution 408 was injected into the system before the feed solution 409 entered the reference flow cell 414 and the flow cell. Various process controls (i.e. P-1, P-2, P-3, P-4 and P-5) may be provided in the system. Optionally, a chiller 417 may be provided to the feed tank 416.

The RO system was operated in a fully-recycled mode whereby bypass, concentrate, and permeate flows were returned to the feed tank 416. Accordingly, a set of microfilters 418 (KAREI, 5 µm and 0.2 µm for concentrate and 0.2 µm for bypass) were installed, for example, downstream of the flow cell 100 to prevent excess bacteria from entering the feed tank 416 and turning the feed tank into an "active bioreactor". The membranes (Dow BW-30) in the flow cell 100 and the reference flow cell 414 were first compacted at a maximum flux (~65 L/m$^2$·h) overnight with Milli-Q water until a stable flux was achieved. Following compaction, the flux was set to the desired value and NaCl solution was added into the feed tank 416 until a desired concentration of 2 g/L was achieved. The system was left to mix for 1.5 hours before adding in Nutrient Broth (NB) solution (Beckton-Dickinson, Difco NB) into the feed tank 416 to provide an average background nutrient concentration of 6.5 mg/L TOC. The biofouling test was initiated by continuous injection of the bacteria stock solution 408 into the flow line at a dilution rate of 1:500 based on the RO crossflow rate. The biofilm was allowed to grow on the RO membranes in the flow cell 100 and the reference flow cell 414. Simultaneously, the first valve 420 that leads to the drain 430 was opened and the second valve 422 was closed as shown in FIG. 4. Then, the dosing of inorganic particles 406 was initiated with colloidal silica (Sigma-Aldrich, Ludox TMA) via the injection port 404 placed in series and after the reference flow cell 414 for 30 minutes at an appropriate dilution ratio to achieve a concentration of 0.2 g/L in the flow cell 100, based on the RO crossflow rate. The retentate was allowed to drain off for 60 minutes before closing the first valve 420 and opening the second valve 422. The draining after the dosing of silica particles into the flow cell 100 is also termed flushing. This helps the silica particles to be removed as much as possible so that the waveform (for example, the amplitude and arrival time of peaks 114 or 116) returns to its initial waveform even though the biofouling layer is still present. The solution in the feed tank 416 was removed and replaced with a fresh solution at the same NaCl and NB concentration during the 60 minutes of drainage of the retentate. The procedure of dosing and draining was repeated daily.

In another experimental condition, dosing and draining was only performed in the initialization of the biofouling test and at the end of the experiment, with the feed tank content routinely tested for total organic carbon (TOC) values and topped up with NB when necessary to achieve constant TOC values.

Figure 11:
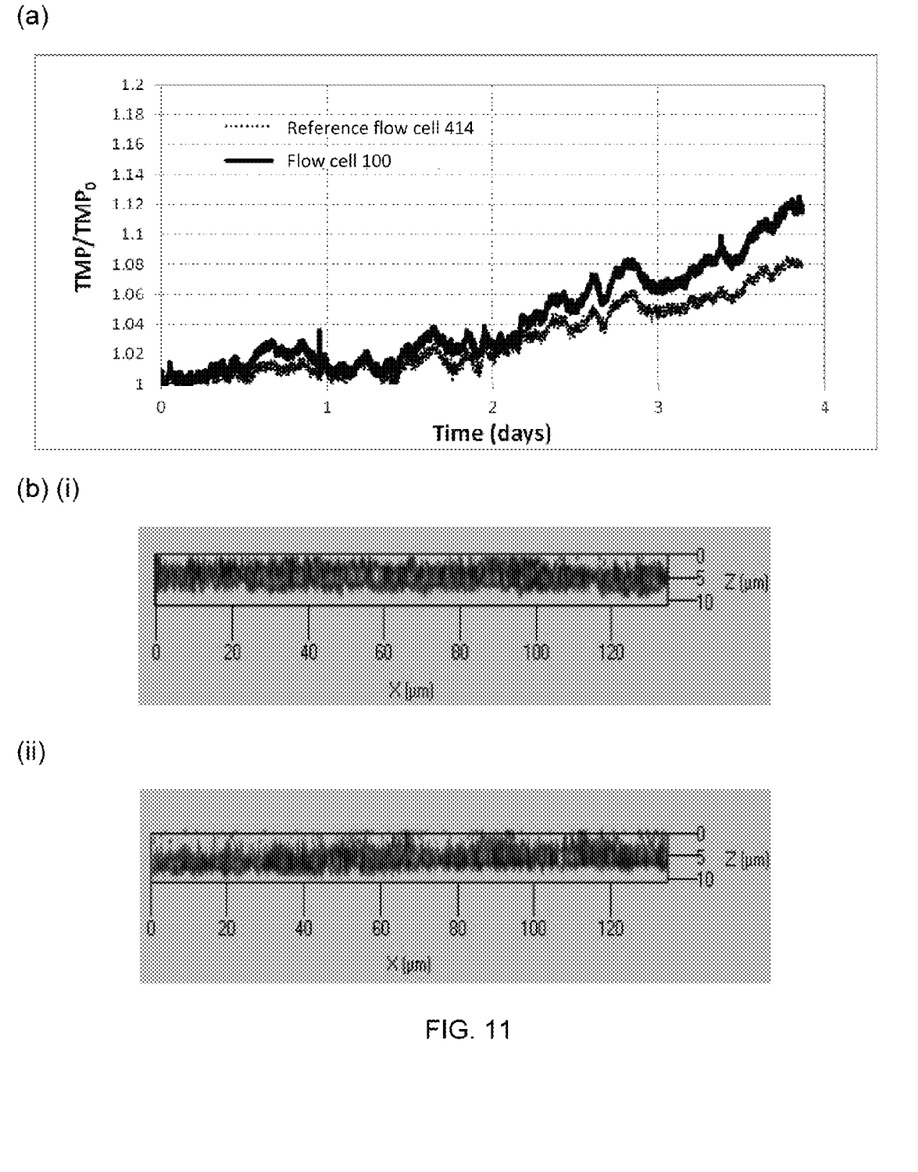
FIG. 11(a) is a graph of $TMP/TMP_0$ measurements as a function of contact time in days for a crossflow velocity of 0.15 m/s, a constant flux of 35 LMH, an aqueous sodium chloride solution of 2 g/L, dilution factor of 500 for model bacteria, for a flow cell with a dosing of silica concentration of 0.2 g/L at initiation and end of a biofouling experiment, and for a reference flow cell.
FIG. 11(b) is corresponding CSLM images of (i) a flow cell membrane sample (Thickness~4 μm) and (ii) a reference flow cell membrane sample (Thickness~4 μm)

During the period of dosing and draining, acoustic measurements were taken at regular intervals. The acoustic measurement system consisted of a 5 MHz ultrasonic transducer 424 (Olympus, Model Ventrascan), a pulser-receiver 426 (Panametrics 5058PR) and a 300 MHz digitizer 428 (National Instruments, Model PCI-5152) with a sensitivity of 0.5 ns/div and 39 my/div. The transducer 424 was externally mounted near the centre of the canary flow cell 100 in contact with a top plate of the flow cell 100 using silicone oil (Olympus, Model C2) as an acoustic coupling agent. At the end of the experiments, biofilms on the membranes in both the flow cell 100 and the reference cell 414 were analyzed for their thickness (as shown in FIG. 11) with a confocal light scanning microscope (CLSM). A specific area where the acoustic transducer was located was cut and separated. Biofilms were prepared for CLSM by staining with the LIVE/DEAD BacLight Bacterial Viability Kits (Molecular Probes, L7012). The preparation method used was in accordance to the manufacturer's specifications, but modified based on the condition of the experiments.

Using UTDR as the analysis methodology, from equation 2 above, thickness of the foulant layer may be calculated from changes in the arrival time of the reflected sound wave. The other analysis methology such as ultrasonic frequency domain reflectometry (UFDR) may also be used.

Experimental Results

Figure 5:
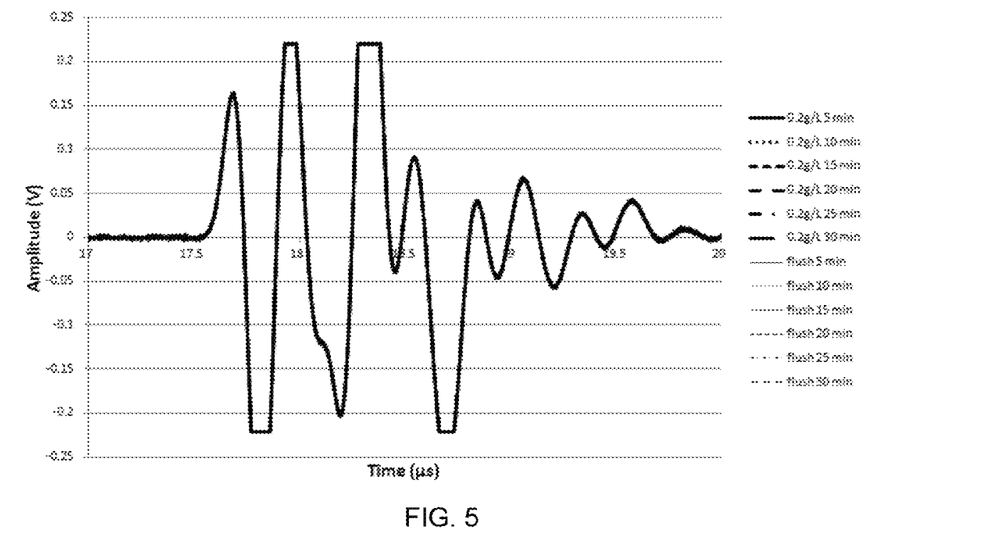
FIG. 5 is a graph of representative amplitude versus arrival time for various signal acquisition times during a dosing and flushing procedure for a crossflow velocity of 0.15 m/s crossflow velocity, a constant flux of 35 LMH, an aqueous sodium chloride solution of 2 g/L, dilution factor of 500 for model bacteria and a dosing of silica concentration of 0.2 g/L at day 4.
Figure 6:
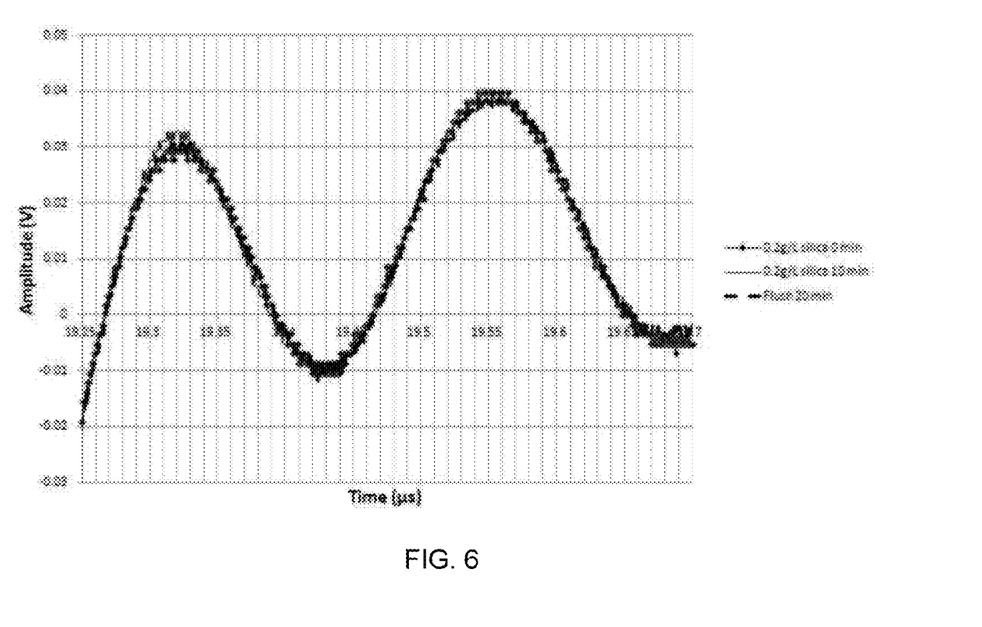
FIG. 6 is a graph of representative amplitude versus arrival time for various signal acquisition times during a dosing and flushing procedure for a crossflow velocity of 0.15 m/s, a constant flux of 35 LMH, an aqueous sodium chloride solution of 2 g/L, dilution factor of 500 for model bacteria and a dosing of silica concentration of 0.2 g/L at initiation of a biofouling experiments.
Figure 7:
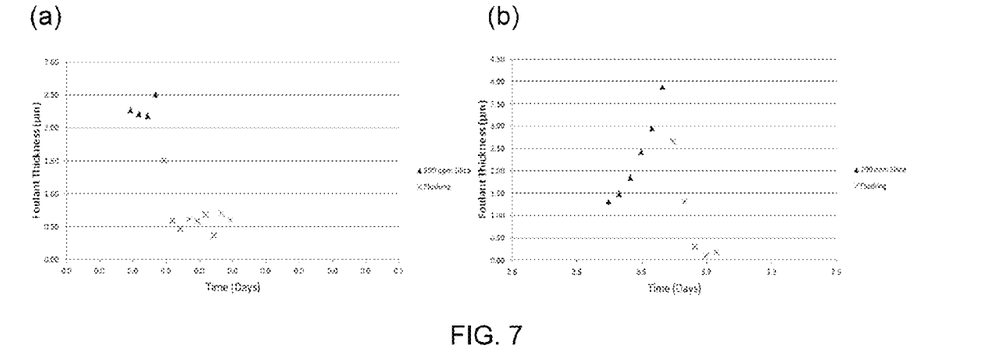
Figure 8:
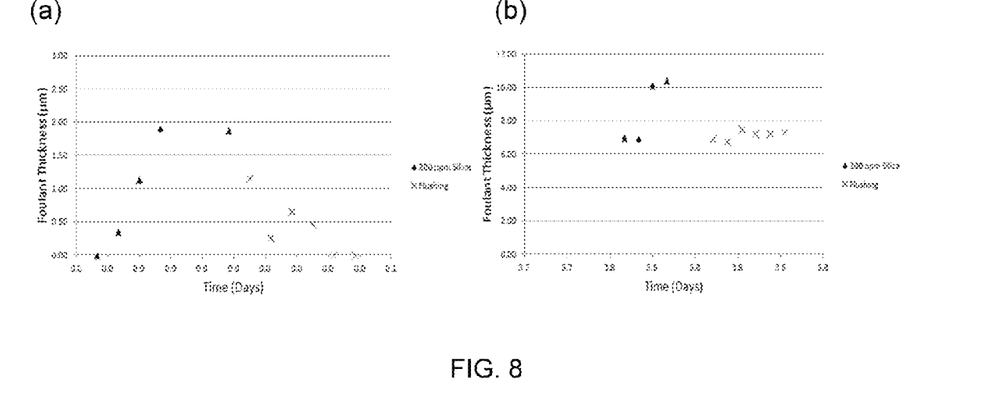
Figure 9:
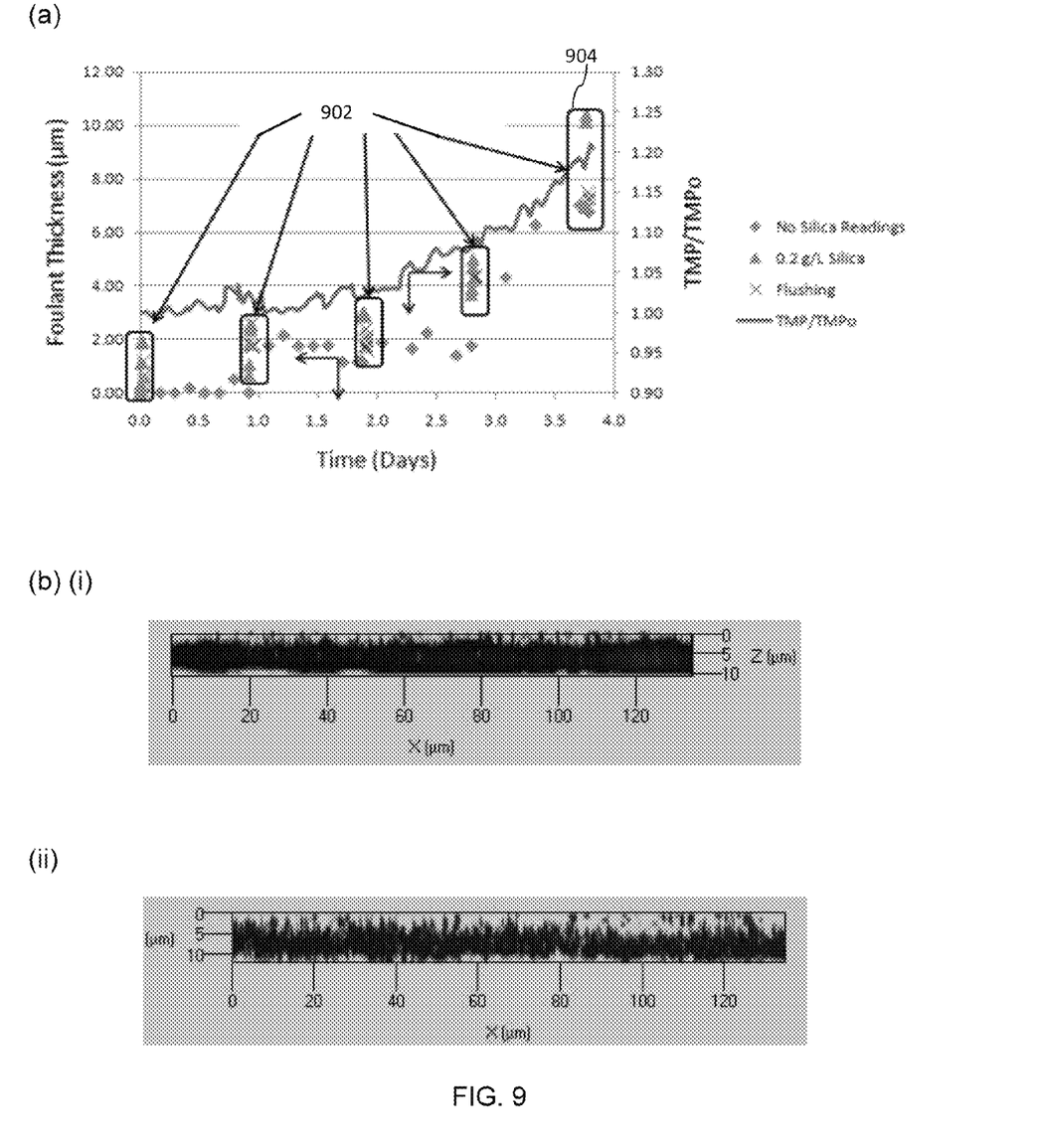
FIG. 9(a) is a graph of fouling layer thickness determined via UTDR and corresponding $TMP/TMP_0$ measurements as a function of contact time in days for a crossflow velocity of 0.13 m/s, a constant flux of 40 LMH, an aqueous sodium chloride solution of 2 g/L, dilution factor of 500 for model bacteria and a daily dosing of silica concentration of 0.2 g/L.
FIG. 9(b) is corresponding CSLM images of two positions on the same membrane of the flow cell: i) position 1 (Thickness~10 μm) and (ii) position 2 (Thickness~8 μm).

FIG. 5 shows a typical plot of the amplitude of the acoustic wave response in volts as a function of the arrival time in microseconds for contact times during the 60 minutes of draining that comprises 30 minutes of dosing of 0.2 g/L of silica and the remaining 30 minutes for flushing. FIG. 6 shows the reversible artificial enhancement of the acoustic impedance on the acoustic signature from the plot of the amplitude of the acoustic wave response in volts as a function of the arrival time in microseconds for contact times during the 60 minutes of drainage. FIGS. 7 and 8 shows the reversible artificial enhancement of the acoustic impedance on the acoustic signature from a plot of the fouling layer thickness determined via UTDR as a function of contact times during the 60 minutes of draining at the initialization of the biofouling experiments and at the end of the experiments for the dosing and flushing procedure for both experimental conditions of daily dosing and the non-daily dosing of silica.

FIG. 9(a) show a plot of the fouling layer thickness determined via UTDR at points 902 of silica dosing and flushing, and the corresponding TMP measurements as a function of contact time for a crossflow velocity of 0.15 m/s and flux of 40 LMH. FIG. 9(b)(i) and (ii) show corresponding CLSM measured thicknesses of two positions on the same membrane of the flow cell 100 respectively, where the thickness for position 1 was about 10 μm and the thickness for position 2 was about 8 μm. The CLSM measured thicknesses are in good agreement with UTDR determined thickness with daily silica dosing after 3.5 days 904. The trend of TMP measurement is also consistent with the UTDR measurement, except for that at the incipient biofouling. This further demonstrates that while TMP measurement is incapable of detecting incipient biofouling, the present method 10 is very sensitive to and capable of detecting initiation of biofouling.

Figure 10:
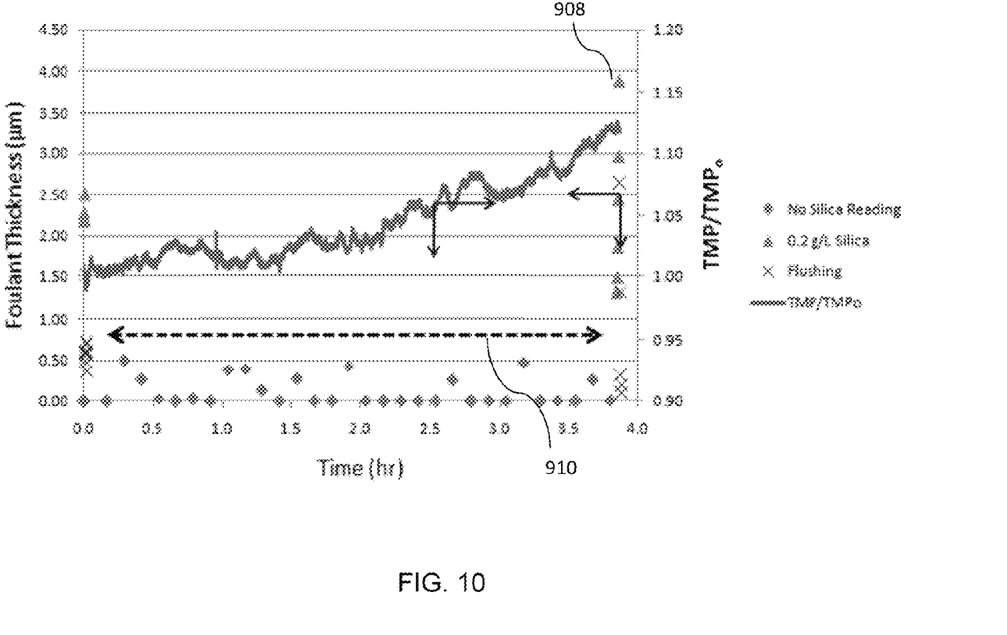
FIG. 10 is a graph of fouling layer thickness determined via UTDR and corresponding $TMP/TMP_0$ measurements as a function of contact time in days for a crossflow velocity of 0.13 m/s, a constant flux of 40 LMH, an aqueous sodium chloride solution of 2 g/L, dilution factor of 500 for model bacteria and a dosing of silica concentration of 0.2 g/L at initiation and end of a biofouling experiment.

FIG. 10 shows a plot of the fouling layer thickness determined via UTDR and the corresponding TMP measurements as a function of contact time for a crossflow velocity of 0.13 m/s and flux of 35 LMH with non-daily dosing of silica, where silica was dosed only at the initiation (time=0 hr) and at the end of the experiment (time=after 3.5 days). FIG. 11 shows a plot of the TMP measurements as a function of contact time for both the canary cell 100 and the reference cell 414 for a crossflow velocity of 0.13 m/s and flux of 35 LMH with non-daily dosing of silica. The corresponding CLSM measured thickness as shown in FIGS. 11(b)(i) and (ii) of fouling for the membrane of the flow cell 100 (about 4 μm) and the membrane of the reference flow cell 414 (about 4 μm) respectively that are in good agreement with UTDR determined thickness 908 shown in FIG. 10 after 3.5 days.

The corroboration of CLSM measurement and the thickness determined via UTDR showed good accuracy of the UTDR measurement and the successful application of inorganic or other appropriate particles to artificially enhance the acoustic impedance of biological or organic fouling. Moreover, the similar fouling trend and the similar thickness measured via CLSM of the two similarly designed RO cells (the flow cell 100 and the reference flow cell 414) showed the negligible influence of the dosing regime (i.e. whether daily or only at the initiation and end of experiment) of the inorganic foulant (i.e. the inorganic particles) to artificially enhance the acoustic impedance of the biological or organic foulant layer, since both daily dosing and initiation-and-end-only dosing both gave UTDR measurements of foulant layer thickness that are well corroborated by CLSM measurements.

Referring to FIG. 10, it should be noted that there is relatively constant and negligible thickness over time determined via UTDR without the presence of silica as can be seen with the readings taken without silica 910. This proves the limitation of the conventional acoustic technique in being unable to detect the biological foulant layer without artificial enhancement via the dosing of inorganic particles.

Whilst there has been described in the foregoing description exemplary embodiments of the present invention, it will be understood by those skilled in the technology concerned that many variations in details of design, construction and/or operation may be made without departing from the present invention. For example, the inorganic particles may be introduced into the flow cell via other appropriate means than the feed solution.

The invention claimed is:

1. A method of determining a state of biofouling of a membrane contained within a flow cell, the flow cell having at least an outer surface coupled to one or more acoustic transducers, the method comprising the following steps:

introducing inorganic particles into the flow cell such that the inorganic particles form at least a part of a top surface of a foulant layer on the membrane;

emitting acoustic waves towards the membrane using the one or more transducers;

detecting an acoustic signature of reflected sound waves, the acoustic signature comprising a profile of reflected sound waves from the top surface and a profile of reflected waves from the membrane; and determining, based on the detected acoustic signature, a state of biofouling of the membrane.

2. The method of claim 1, wherein the membrane is a flat sheet membrane.

3. The method of claim 1, wherein the acoustic signature further comprises a profile of reflected sound waves from a reference point.

4. The method of claim 3, wherein the step of determining comprises comparing the profile of reflected sound waves from the top surface and the profile of reflected sound waves from the membrane against the profile of reflected sound wave from the reference point.

5. The method of claim 1, wherein the step of determining further comprises analysing the acoustic signature using ultrasonic time domain reflectometry.

6. The method of claim 1, wherein the state of biofouling comprises at least one of: a thickness of the foulant layer, the rate at which biofouling occurs, and the amount of membrane compaction.

7. The method of claim 1, wherein the inorganic particles comprise particles capable of enhancing an acoustic impedance difference between the foulant layer and the membrane.

8. The method of claim 1, wherein the inorganic particles comprise particles capable of enhancing an acoustic impedance difference between the foulant layer and the feed solution.

9. The method of claim 1, wherein the inorganic particles comprise at least one of: silica particles, nanoparticles, glass beads, and a colloidal insoluble compound.

10. The method of claim 1, wherein the step of introducing inorganic particles comprises one of: intermittently injecting, partially injecting and continuously injecting the inorganic particles.

11. The method of claim 1, wherein the acoustic transducer is a focused transducer.

12. The method of claim 1, further comprising a step of removing the inorganic particles from the flow cell.

13. The method of claim 1, comprising repeating the method with the step of claim 12.

14. A method of determining a state of biofouling of a first membrane in a membrane module, the method comprising the steps of:

providing an ancillary flow cell comprising a second membrane in parallel with the membrane module;

diverting part of a feed stream for the membrane module as a side stream into the ancillary flow cell;

introducing inorganic particles into the ancillary flow cell such that the inorganic particles form at least a part of a top surface of a foulant layer formed on the second membrane due to the side stream;

emitting acoustic waves towards the second membrane using at least one transducer;

detecting an acoustic signature of reflected acoustic waves, the acoustic signature comprising a profile of reflected sound waves from the top surface and a profile of reflected sound waves from the second membrane;

determining, based on the detected acoustic signature, a state of biofouling of the second membrane; and configuring the ancillary flow cell relative to the membrane module such that a state of biofouling of the ancillary flow cell is indicative of a state of biofouling of the first membrane in the membrane module.

15. The method of claim 14, wherein the second membrane is a flat sheet membrane.

16. The method of claim 14, wherein the acoustic signature further comprises a profile of reflected sound waves from a reference point.

17. The method of claim 14, wherein the step of determining comprises comparing the profile of reflected sound waves from the top surface and the profile of reflected sound waves from the membrane against the profile of reflected sound wave from the reference point.

18. The method of claim 14, wherein the step of determining further comprises analysing the acoustic signature using ultrasonic time domain reflectometry.

19. The method of claim 14, wherein the state of biofouling comprises at least one of: a thickness of the foulant layer, the rate at which biofouling occurs, and the amount of membrane compaction.

20. The method of claim 14, wherein the inorganic particles comprise particles capable of enhancing an acoustic impedance difference between the foulant layer and the second membrane.

21. The method of claim 14, wherein the membrane module is one of: a spiral wound module and a hollow fiber membrane module.

22. The method of claim 14, wherein the ancillary flow cell is configured to foul earlier than the membrane module.

23. The method of claim 14, further comprising removing the inorganic particles from the ancillary flow cell.

24. An apparatus for determining a state of biofouling of a first membrane in a membrane module, the apparatus comprising:

an ancillary flow cell configured to receive part of a feed stream diverted from the membrane module, the ancillary flow cell comprising a second membrane provided in a compartment defined between a top plate and a bottom plate;

inorganic particles configured to be introduced into the ancillary flow cell to form at least a part of a top surface of a foulant layer formed on the second membrane;

at least one transducer provided on at least one of: the top plate and the bottom plate, the at least one transducer configured to emit acoustic waves towards the second membrane and to receive reflected waves from the top surface and reflected waves from the second membrane; and an analysis module configured to perform acoustic reflectometry measurements and to determine a state of biofouling of the ancillary flow cell based on acoustic signatures of the reflected waves from the top surface and reflected waves from the second membrane;

such that a state of biofouling of the ancillary flow cell is indicative of a state of biofouling of the first membrane in the membrane module.

25. The apparatus of claim 24, wherein the second membrane is a flat sheet membrane.

26. The apparatus of claim 24, wherein the state of biofouling comprises at least one of: a thickness of the foulant layer, the rate at which biofouling occurs, and the amount of membrane compaction.

27. The apparatus of claim 24, wherein the inorganic particles comprise particles capable of enhancing an acoustic impedance difference between the foulant layer and the second membrane.

28. The apparatus of claim 24, wherein the ancillary flow cell is configured to foul earlier than the membrane module.

* * * * *